United States Patent [19]

Smith et al.

[11] Patent Number: 4,493,899

[45] Date of Patent: Jan. 15, 1985

[54] METHOD OF TESTING FOR PARTICULAR ANTIBODIES IN THE SERUM OF A PATIENT

[75] Inventors: Lloyd H. Smith, Davis; Raymond L. Teplitz, Pasadena, both of Calif.

[73] Assignee: City of Hope, Duarte, Calif.

[21] Appl. No.: 312,159

[22] Filed: Oct. 16, 1981

[51] Int. Cl.³ .................. G01N 33/54; G01N 33/56; C12Q 1/44; C12Q 1/68

[52] U.S. Cl. ........................... 436/508; 436/513; 436/518; 436/543; 436/804; 436/811; 436/823; 436/824; 436/825; 435/6; 435/7; 435/19

[58] Field of Search ............ 424/1.1, 1, 1.5; 23/230 B; 436/518–535, 94, 811, 513, 825, 508, 543, 823, 804, 824; 435/4, 6, 7, 19

[56] References Cited

U.S. PATENT DOCUMENTS

| | | | |
|---|---|---|---|
| 3,992,517 | 11/1976 | Lowke et al. | 424/12 |
| 4,189,464 | 2/1980 | Blumberg et al. | 424/1 |
| 4,234,563 | 11/1980 | Rippe | 424/8 |
| 4,251,514 | 2/1981 | Rippe | 424/8 |
| 4,267,270 | 5/1981 | Stout | 435/7 |
| 4,273,756 | 6/1981 | Ling et al. | 424/1 |

OTHER PUBLICATIONS

Heinzerling, R. H. et al., J. Investigative Dermatology, vol. 75(3), pp. 224–227 (1980).

Miller, Thomas E., Arthritis-Rheumatism, vol. 24(4), pp. 602–610 (4-1981).

Okudaira, Hirokazu et al., J. Immunological Methods, vol. 41, (pp. 201–213 (3-1981).

Hashimoto, H. et al., Nippon Rinsho, vol. 37(2), pp. 452–462 (1979).

Aarden, Lucien A. et al., *Immunological Methods*, vol. II, pp. 75–82 (1981).

Adam, C. et al., J. of Immunological Methods, vol. 27, pp. 133–143 (1979).

Fish, Falk et al., Fed. Proceedings, vol. 39(3), p. 472 (1980) and Arthritis & Rheumatism, vol. 24(3), pp. 534–543 (1981).

Harrington, John T. et al., Arthritis & Rheumatism, vol. 19(4), p. 801 (1976).

Lange et al., Clinical-Experimental Immunology, vol 25(2), pp. 191–198 (1976).

Smith et al., Journal of Laboratory-Clinical Medicine, vol. 98, (3), pp. 425–436 (1981).

*Primary Examiner*—Benjamin R. Padgett
*Assistant Examiner*—M. Moskowitz
*Attorney, Agent, or Firm*—Ellsworth R. Roston; Charles H. Schwartz

[57] ABSTRACT

A method is provided for testing for particular antibodies in the serum of a patient. The antibodies may be those of systemic lupus erythematosus and may constitute IgG and IgM immunoglobulins. The IgG and IgM immunoglobulin may be individually labeled radioactively.

An antigen (such as DNA) may be attached to a support such as sepharose. The attachment may be facilitated as by irradiation with ultraviolet light. The DNA may be single stranded or double stranded. When double-stranded DNA is used, single-stranded portions in the double strands may be removed as by a suitable enzyme.

The particular antibodies may be attached to the antigen such as the supported DNA. An assay may then be provided to determine the attachment of the particular antibodies to the supported DNA. When the particular antibodies constitute immunoglobins of systemic lupus erythematosus, the assay may actually provide a determination of the amounts of the IgG and IgM immunoglobulins individually attached to the single-stranded and double-stranded DNA.

33 Claims, 7 Drawing Figures

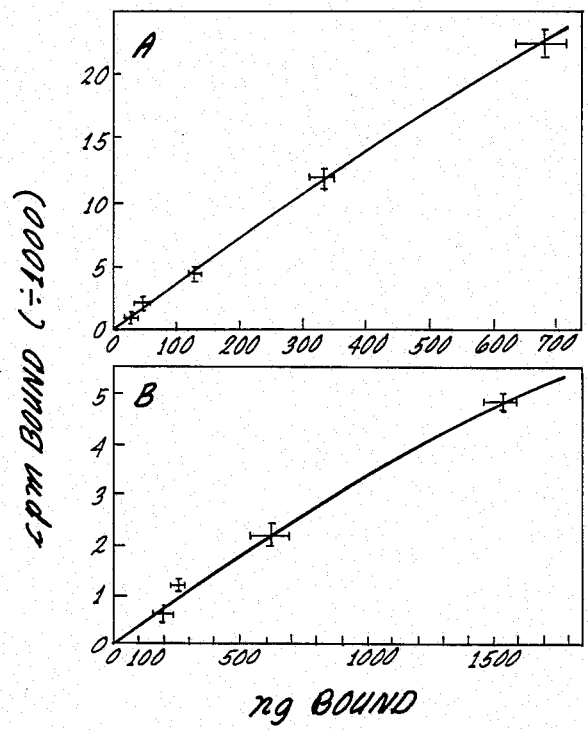

TABLE I NATIVE DNA-BINDING IMMUNOGLOBULINS IN A NORMAL CONTROL SERUM POOL

| | AVERAGE ± S.D. | | | | UNDILUTED SERUM ($\mu g/ml$)† |
|---|---|---|---|---|---|
| | $B_N$ (cpm) | $S_N$ (cpm) | PAIRED DIFFERENCE (cpm) | p VALUE | |
| IgM | 759 ± 104 | 952 ± 153 | 193 ± 50 | <0.01 | 0.7 ± 0.2 |
| IgG | 3614 ± 743 | 3973 ± 888 | 354 ± 149 | <0.05 | 0.1 ± 0.05 |

Fig. 6

TABLE II DENATURED DNA-BINDING IMMUNOGLOBULINS IN A NORMAL CONTROL SERUM POOL

| | AVERAGE ± S.D. | | | | UNDILUTED SERUM ($\mu g/ml$) |
|---|---|---|---|---|---|
| | $B_D$ (cpm) | $D$ (cpm) | PAIRED DIFFERENCE (cpm) | p VALUE | |
| IgM | 485 ± 61 | 1739 ± 75 | 1303 ± 48 | <0.001 | 5.5 ± 0.2 |
| IgG | 990 ± 195 | 7798 ± 532 | 6808 ± 425 | <0.001 | 5.0 ± 0.3 |

FIG. 7

TABLE III SERUM ANTIBODY LEVELS (μg/ml)

| PATIENT NO | AGE (yr) | SEX | IgG DS | IgG SS | IgM DS | IgM SS | CATEGORY |
|---|---|---|---|---|---|---|---|
| 1 | 23 | F | 138 | 51 | 51 | 52 | ALL FOUR ANTIBODY LEVELS ELEVATED (n=19) |
| 2 | 26 | F | 73 | 107 | 18 | 23 | |
| 3 | 46 | F | 87 | 57 | 6.6 | 10 | |
| 4 | 50 | F | 38 | 41 | 65 | 70 | |
| 5 | 34 | F | 43 | 72 | 4.7 | 33 | |
| 6 | 31 | F | 12 | 80 | 16 | 38 | |
| 7 | 23 | F | 17 | 25 | 34 | 92 | |
| 8 | 22 | F | 16 | 42 | 3.8 | 74 | |
| 9 | 40 | F | 2.8 | 15 | 13 | 23 | |
| 10 | 26 | M | 8 | 30 | 3 | 16 | |
| 11 | 29 | F | 6.7 | 42 | 12 | 110 | |
| 12 | 24 | F | 12 | 23 | 4 | 17 | |
| 13 | 21 | F | 19 | 10 | 4.2 | 17 | |
| 14 | 29 | F | 7.6 | 37 | 10 | 32 | |
| 15 | 32 | F | 7 | 28 | 4 | 24 | |
| 16 | 23 | F | 7.1 | 29 | 6 | 28 | |
| 17 | 35 | F | 3.8 | 12 | 7.6 | 35 | |
| 18 | 36 | F | 2.3 | 15 | 7.8 | 24 | |
| 19 | 19 | F | 1 | 40 | 1.5 | 37 | |
| 20 | 34 | F | 14 | 27 | <1 | 16 | THREE ANTIBODY LEVELS ELEVATED (n=7) |
| 21 | 55 | F | <1 | 25 | 3.3 | 20 | |
| 22 | 67 | F | 3.8 | 7.6 | 2.3 | 12 | |
| 23 | 22 | F | 5 | 9.5 | 6.6 | 6.6 | |
| 24 | 40 | F | <1 | 13 | 6 | 46 | |
| 25 | 36 | F | <1 | 32 | 3.3 | 24 | |
| 26 | 32 | F | <1 | 34 | 4.7 | 23 | |
| 27 | 22 | F | 9 | 29 | <1 | 3.5 | TWO ANTIBODY LEVELS ELEVATED (n=5) |
| 28 | 27 | F | <1 | 15 | <1 | 106 | |
| 29 | 38 | F | <1 | 7.6 | 6 | 38 | |
| 30 | 33 | M | 8.5 | 28 | <1 | <1 | |
| 31 | 70 | F | 3.8 | 14 | <1 | 4.7 | |
| 32 | 55 | M | <1 | 36 | <1 | 4 | ONE ANTIBODY LEVEL ELEVATED (n=3) |
| 33 | 61 | F | 8 | 6.6 | 1 | 5.7 | |
| 34 | 25 | F | 1.4 | 3.8 | <1 | 2.8 | |
| 35 | 37 | M | <1 | 3.8 | <1 | 4.7 | ALL ANTIBODY LEVELS NORMAL (n=3) |
| 36 | 35 | F | <1 | 4.2 | <1 | 2 | |
| 37 | 25 | M | <1 | 2.8 | <1 | 3.8 | |

METHOD OF TESTING FOR PARTICULAR ANTIBODIES IN THE SERUM OF A PATIENT

This invention relates to methods of providing assays of antibodies in the serum of a patient and more particularly relates to methods of attaching such antibodies to antigens attached to a support and of then providing such assays. The invention is particulary adapted to attach antibodies of systemic lupus erythematosus to supported antigens such as DNA.

As diseases progress in the body of a patient, the amount of antibodies produced by such diseases tends to increase. Sometimes even more than one antibody exists in a patient when the disease exists in the patient. Furthermore, the amount of one of the antibodies may increase in the patient relative to the amount of the other antibody in the patient as the disease progresses. For example, the IgG and IgM immunoglobulins may exist in a patient when the patient has systemic lupus erythematosus. The IgG and IgM immunoglobulins tend to increase at different rates in the patient as the disease of systemic lupus erythematosus progresses in the patient.

A considerable effort has been made over the last several years to provide assays of antibodies in a patient. Such efforts have not been very quantitatively successful. For example, efforts have been made to isolate and assay the immunoglobulins of systemic lupus erythematosus in a patient. As of this date, no one has been able to provide successfully a quantitative measurement of the antibodies of systemic lupus erythematosus.

This invention provides a method of attaching antigens to a support and then attaching antibodies of systemic lupus erythematosus to the antigens for providing an assay of the attached antibodies. The invention further provides a method of attaching antibodies (other than systemic lupus erythematosus) to be supported DNA to provide an assay.

In one embodiment of the invention, a method is provided for testing for particular antibodies in the serum of a patient. The antibodies may be those of systhamatous lupus erythamatosus and may constitute IgG and IgM immunoglobulins.

An antigen (such as DNA) may be attached to a support such as Sephadex (made by Pharmacia). The attachment may be facilitated as by irradiation with ultraviolet light. The DNA may be single stranded or double stranded. When double-stranded DNA is used, single-stranded portions in the double strands may be removed as by a suitable enzyme.

The particular antibodies may be attached to the antigen such as the supported DNA. An assay may then be provided to determine the attachment of the particular antibodies to the supported DNA. When the particular antibodies constitute immunoglobulins of systemic lupus erythematosus, the assay may actually provide a determination of the amounts of the IgG and IgM immunoglobulins individually attached to the single-stranded and double-stranded DNA.

Figure 1A:
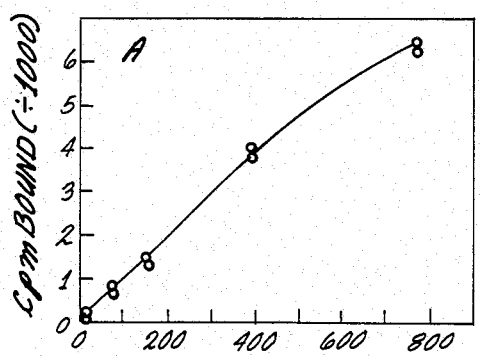
FIGS. 1A and 1B are curves respectively illustrating the rate at which IgG and IgM immunoglobulins become bound to supported DNA.

FIGS. 4A and 4B constitute curves illustrating the rate at which the IgG and IgM immunoglobulins become bound to DNA when the immunoglobulins are provided with particular dilutions;

FIG. 5 constitutes a table illustrating the attachments of the IgG and IgM immunoglobulins to supported native (double-stranded) DNA and to the support without DNA;

FIG. 6 constitutes a table illustrating the attachments of the IgG and IgM immunoglobulins to supported denatured (single-stranded) DNA and to the support with DNA; and FIG. 7 illustrates the amount at which the IgG and IgM immunoglobulins from different patients become attached to the supported native DNA, the supported denatured DNA and the supports from which the native and denatured DNA have been removed.

The methods disclosed and claimed in this patent application are also described in detail in an article entitled "A quantitative radioimmunoassay for DNA-binding antibodies" and prepared by Lloyd H. Smith, Ruth L. Guyer, Ronald M. Minami and Raymond L. Teplitz and published in the Journal of Laboratory and Clinical Medicine in September, 1981.

Abbreviations Sle (SLE), phosphate-buffered saline without calcium or magnesium salts (PBS-A), goat anti-human (GAH), ethylenediamine tetraacetic acid (EDTA), ethyleneglycol-his-(aminoethyl ether), N,N$^1$-tetraacetic acid (EGTA), bovine serum albumin (BSA), Internatonal Reference Serum (serum IRP), radial immunodiffusion (RID), radioimmunoassay (RIA), sodium dodecyl sulfate (SDS), ultraviolet (UV), counts per minute (cpm).

Subjects. Blood samples from SLE patients and normal control patients were obtained by venipuncture and allowed to clot at room temperature. Plasma was obtained into acid-citrate-dextrose from several patients by plasmapheresis. Sera and plasma were stored at $-20°$ C. Whenever possible, fasting sera were used, and all sera were centrifuged to remove particulate matter and lipid.

Buffers. Buffer A was PBS-A (0.15 M NaCl, 0.0003 M KCL, 0.002 M Na$_2$HPO$_4$, 0.001 M KH$_2$PO$_4$) at pH 7.5, containing 0.5 mM Na$_3$EGTA, 0.5 mM Na$_3$EDTA, and 5% glycerol. Buffer B was the same as buffer A and, in addition, contained 1 mg/ml BSA (reagent grade; Pentex, Inc., Kankakee, Ill.). Buffer C was the same as buffer B but contained Na$_3$EDTA and Na$_3$EGTA at 5 mM each.

Enzymes:

1. DNAse 1 (Sigma Chemical Co., St. Louis, Mo.), 50 g/ml, prepared in PBS-A at pH 7.5 containing 12 mM MgCl$_2$.
2. S$_1$ nuclease, 30 U/g of DNA, in 0.033 M sodium acetate, pH 4.5, 0.3 M NaCl, and 0.1 mM ZnSO$_4$.

DNA purification. High molecular-weight calf thymus DNA (type I: Sigma) was dissolved at 4 to 5 mg/ml in 0.2 M Tris HCl (pH 7.4)-0.05 M Na$_3$EDTA and treated in the following way to remove residual protein. SDS was added to a final concentration of 1% and proteinase K (EM Laboratories, Inc., Elmsford, N.Y.) was added to give a final concentration of 200 g/ml. The solution was incubated for 16 to 20 hr. at 37° C. and was then extracted twice with chloroform-isoamyl alcohol (24:1). DNA was recovered by spooling after addition of 2 vol. of absolute ethanol. The DNA was further washed twice in 2 L of 70% ethanol, allowed to dry in air, and dissolved in 5 mM Tris HCl (pH 7.5)-0.5 mM Na$_3$EDTA to a final concentration of approximately 3 mg/ml.

Measurement of immunoglobulins. Total serum IgG and IgM were measured by RID.

$^{135}$I and $^{125}$I labeling. $^{131}$I and $^{125}$I were obtained from ICN Pharmaceuticals, Covina, Calif. Protein iodination using chloramine T was performed as described by McConahey and Dixon in "A Method of Trace Iodination of Proteins for Immunologic Studies" at 29 Int. Arch. Allergy 285 in 1966. Unincorporated iodide was removed by one-step filtration through Sephadex PD-10 columns (Pharmacia Fine Chemicals, Piscataway, N.J.) equilibrated with buffer B. Antibodies labeled to specific activity of 1 Ci/g showed no loss of activity during storage at 4° C. for up to 6 weeks.

Miscellaneous reagent. The S$_1$ nuclease was obtained from Miles Laboratories, Inc., Elkhart, Ind. GAH IgG (gamma chain-specific) and GAH IgM (mu chain-specific) solid phase-absorbed antisera and solid phase-prepared pure antibody were obtained from Tago, Inc., Burlingham, Calif. Serum IRP 67/95 was obtained from National Cancer Center Immunodiagnostic Reference Center, Springfield, Va. The serum IRP was reconstituted with 1 ml of water at room temperature and briefly centrifuged to remove particulate material.

The purified DNA was then attached to a support such as a sephadex. The sephadex may be in the form of a powder and may be identified by the trademark "Sephadex". Such sephadex has advantages because it is relatively fine and is capable of providing an efficient attachment to the DNA. The attachment of the DNA to the sephadex powder may be facilitated by radiation of the DNA and the powder with ultraviolet light. The DNA may be native (double-stranded) or denatured (single-stranded). When the DNA is native (double-stranded), the DNA generally contains portions that are single-stranded. These portions are preferentially removed by treatment with the enzyme designated as S$_1$ nuclease.

The attachment of the DNA to the sephadex powder may be accomplished by a modification of a method described by R. Litman in "A deoxyribonucleic acid polymerase from Micrococcus luteus (Micrococcus lysodeiktious) isolated deoxyribonucleic acid-cellulose" at 243 J. Biol. Chem 6222 in 1968. The method used is set forth below:

DNA-Sephadex preparation. Fifty grams of Sephadex G-50 Superfine (Pharmacia) were swollen in 2 mM Tris HCl (pH 7.4)-0.5 mM EDTA; the 250 mg/ml native (double-stranded) or denatured (single-stranded) DNA were added to aliquots of filtered Sephadex cake. Each batch was throughly mixed, dried and lyophilized. This was ground to a fine powder and passed through a No. 80 stainless steel sieve (pore size 180 μm). The powder was suspended in 2 gm aliquots in 40 ml of absolute ethanol and stirred during irradiation with UV light (total dose approximately 160,000 erg/mm$^2$). The irradiated DNA-Sephadex was then dried on a Buchner funnel, reground briefly to break up aggregates, and suspended in 2 L. of buffer A. After several washes with buffer A, the DNA-Sephadex was stored at 4° C.

The DNA content was determined with DNAse 1 as follows. An aliquot equivalent to 1 ml packed volume of DNA-Sephadex was thoroughly washed with PBS-A and then incubated in 4 ml of buffer C (contains DNAse 1) at 37° C. for 30 min. After centrifugation, the supernatant was diluted and its absorption at 260 nm was measured. The mass of DNA eluted was calculated assuming 1.0 A$_{260}$ unit per 0.04 mg of digested DNA. Approximately 0.5 to 1 mg of native DNA and 1 to 2 mg of denatured DNA were bound per packed milliliter of swollen DNA-Sephadex. Prior to use in the DNA-Sephadex assay, the washed native and denatured DNA-Sephadex preparations were adjusted to 50% suspensions. A volume (one fifth of the total) of a swollen 50% suspension of DNA-free Sephadex G-50 superfine in buffer A was added to each; the uncoupled Sephadex beads made the DNA-Sephadex pellets more stable during subsequent steps.

The native DNA-Sephadex preparation was divided in half. One half was treated with S$_1$ nuclease in S$_1$ buffer (for conditions see Results and Discussion); the other half was incubated with DNAse 1 for 2 hr. at 37° C. After thorough washing with buffer A, each preparation was allowed to settle in a graduated cylinder; the final suspensions were adjusted to 70%. The S$_1$-treated Sephadex (designated S$_1$N) retained double-stranded DNA; the DNAse 1-treated Sephadex (designated B$_N$) contained no DNA and served as a background control.

The denatured DNA-Sephadex preparation was divided in half. One half was incubated for 2 hr. at 37° C. in buffer A, and the other half was incubated with DNAse 1. These were thoroughly washed and adjusted to 70% suspensions (designated D and B$_D$ DNA-Sephadex). The B$_D$ DNA Sephadex contained no DNA and served as a background control.

After the formation of the sephadex-supported DNA, the treated serum from the patient was added to obtain an attachment of particular antibodies in the serum to the supported DNA. In the reduction of this invention to practice, the serum from the patient contained the IgG and IgM immunoglobulins in at least some instances.

DNA-Sephadex assay for DNA-binding immunoglobulins. Prior to assay, 0.5 ml aliquots of the 70% S$_1$N, B$_N$ and D and B$_D$ DNA-Sephadex suspensions were added to 10 ml of buffer B in 16 by 125 mm plastic screw cap tubes (Falcon Laboratories Division, Becton Dickinson & Co., Oxnard, Calif.). These were mixed and centrifuged at 2000 rpm for 6 min. at room temperature. The supernatants were carefully aspirated and discarded. Serum or plasma to be assayed for immunoglobulins capable of binding to double-stranded DNA was diluted 1:10 buffer C, and 1 ml samples were added to each of the S$_1$N and B$_N$ tubes. Hightiter sera could be further diluted with buffer B when necessary Dilutions of a standard SLE plasma (PS 33076) were also assayed in duplicate with each experiment for construction of standard curves. Tubes were incubated in a gyratory water bath at 37° C. for 2 hr. and centrifuged as above. The supernatants from the B$_N$ tubes were aspirated and discarded. Those of the S$_1$N tubes were transferred to glass tubes for subsequent assay on D DNA-Sephadex. The pelleted S$_1$N and B$_N$ samples were washed twice at room temperature with 10 ml of buffer B; the quantity of bound immunoglobulin was measured by RIA. To each pellet was added 1 ml of a mixture of GAH antibody (200,000 cpm/ml each of $^{125}$I-GAH IgG and $^{135}$I-GAH IgM) plus carrier antisera (anti-IgG at 1:100 and anti-IgM at 1:50). Suspensions were mixed, incubated 1 hr. at 37° C. with agitation, washed twice with 10 ml of buffer B, and counted for $^{125}$I and $^{131}$I in a two-channel Beckman Gamma 7000 counter (Beckman Instruments, Inc., Fullerton, Calif.). Usually the GAH IgG antibody was labeled with $^{125}$I and GAH IgM with $^{131}$I. These labels were sometimes reversed, as indicated in the figure legends.

To assay for immunoglobulins capable of binding to single-stranded DNA, the supernatants from the $S_1N$ first were centrifuged, and 0.2 ml of the supernatant was transferred to plastic tubes containing washed aliquots of D and $B_D$ DNA-Sephadex. Buffer B (0.6 ml) was added to make a final volume of 1 ml. The suspensions were mixed, incubated 2 hr. at 37° C. with agitation, washed twice, and treated with 1 ml of the antibody/antiserum mixture as outlined above. A set of control assays using buffer in place of serum was run with each assay set. These controls lacking serum were designated NS/$S_1$N, NS/$B_N$ and NS/$B_D$.

Calculation of results included the following steps:
1. Correction for $^{131}$I to $^{125}$I counting overlap.
2. Subtraction of blank values (i.e., [$S_1N$-$B_N$] and [D-$B_D$]).
3. Subtraction of background cpm bound due to DNA-binding material present in the $^{125}$I-GAH, IgG and $^{131}$I-GAH IgM antibody preparations (i.e., [NS/$S_1$N-NS/$B_N$] or [NS/D-DN/$B_D$]).
4. Correction for original dilution and for volume differences resulting from partial utilization of the $S_1N$ supernatant in the D DNA-Sephadex assay.

The final cpm values for test sera reflected the amount of human antibody bound to the DNA on the $S_1D$ or D DNA-Sephadex.

Figure 2:
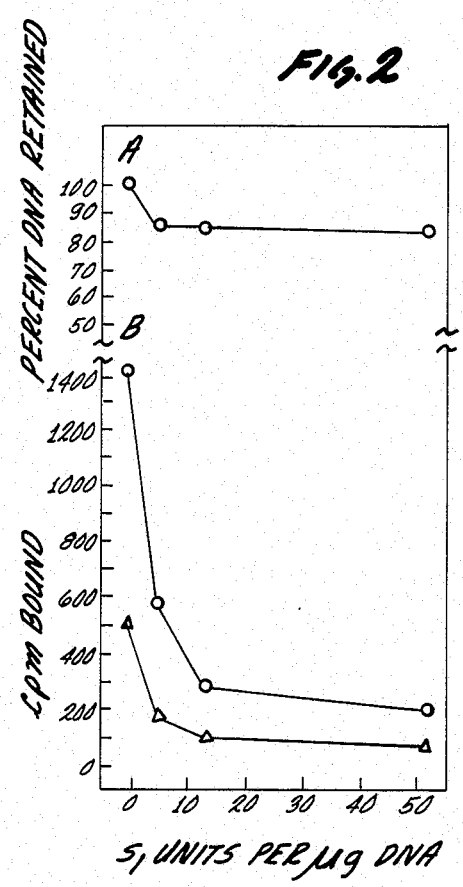
FIG. 2 shows curves illustrating the rate at which IgG and IgM immunoglobulins become bound to supported DNA with different amounts of the nuclease $S_1$ and further illustrating the percent of DNA retained with different amounts of the nuclease $S_1$.

As will be seen from the above discussion, the native (double-stranded) DNA was treated with the single-strand nuclease $S_1$ to remove the single-stranded portions of such DNA. The attachment of the radioactively labeled IgG and IgM immunoglobulins to such relatively pure double-stranded DNA was then individually measured. The data of FIG. 2 show that the preparative conditions of the treatment of the double-stranded DNA by the nuclease $S_1$ were sufficient to remove the major fraction of the DNA that was attached to the Sephadex by regions of single-stranded DNA. This may be seen from the fact that the use of increased levels of the nuclease $S_1$ resulted in the release of very little additional amounts of DNA in FIG. 2.

Figure 3:
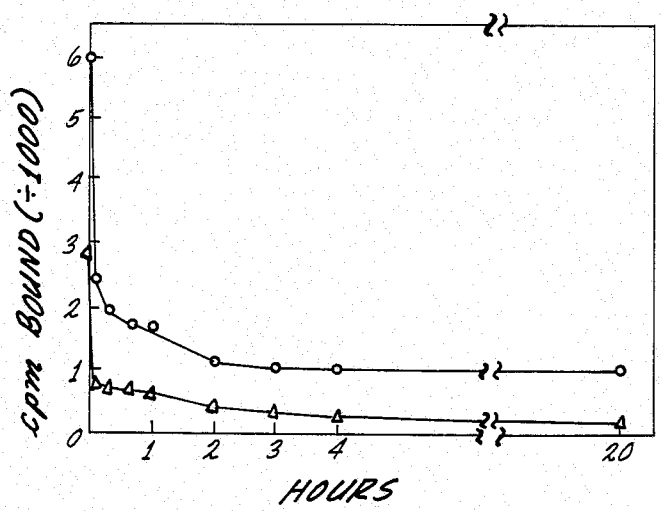
FIG. 3 illustrates the rate at which the immunoglobulins become bound to native DNA with progressive instants of time.

FIG. 3 shows that most of the immunoglobulins binding to native DNA reacted within 5 minutes and were removed from the supernatant, although an additional amount of IgG and IgM immunoglobulin became bound to the $S_1N$ during the subsequent 2 hours. Thus the standard assay conditions involved a 2 hour, 37° C. incubation. The kinetics of binding of immunoglobulins from SLE sera and normal sera to D DNA-Sephadex were very similar to those shown in FIG. 3. FIG. 4 shows representative standard curves for DNA-binding IgG (FIG. 4A) and IgM (FIG. 4B) constructed with Ps 33076 dilutions.

Sixteen independently prepared 1:10 dilutions of a normal human serum pool from five donors were assayed by the standard method for detecting DNA-binding IgM and IgG, thus generating 16 $S_1N$-$B_N$ paired cpm values. The results were evaluated with Student's test for the case of paired variates. FIG. 5 shows that very small, but statistically significant, values were obtained for the average $S_1N$-$B_N$ cpm difference for both IgM and IgG. Interpolating on the standard curve reveals that concentrations of 0.7 g/ml IgM and 0.1 g/ml IgG were present in undiluted serum capable of binding double-stranded DNa. These data represent imunological assignments of 0.04% of the total IgM and 0.001% of total IgG.

FIG. 6 shows the results of the 16 assays of the normal human serum pool for denatured DNA run on the supernatants taken from $S_1N$ assays. Undiluted serum from this pool contained 5.5 g/ml IgM and 5.0 g/ml IgG capable of binding to denatured DNA, or immunological assignments of 0.22% of the total IgM and 0.05% of the total IgG.

The attachment of the radioactively labeled IgG and IgM immunoglobulins to the denatured single-stranded DNA was also individually measured. Corrections were then made for the portions of the denatured DNA that were actually double-stranded. In this way, the attachment of the IgG and IgM immunoglobulins to the single-stranded DNA was determined.

No attempt was made to measure the amount of contaminant double-stranded DNA present in the denatured (single-stranded) DNA-Sephadex preparations. Considering the high concentrations of denatured DNA used, the time during drying with the Sephadex beads, and the ubiquitous presence of inverted repeat regions in eukaryotic DNA preparations, it is expected that some double-stranded DNA is present in the denatured DNA-Sephadex. Therefore, in order to minimize the effect of this contaminating double-stranded DNA on the measurement of immunoglobulin binding to single-stranded DNA, serum was first absorbed with $S_1N$ and then the supernatants were added to D and $B_D$ DNA-Sephadex. Thus, antibodies capable of binding to double-stranded DNA were removed before assay of D DNA-Sephadex by the first-phase absorption of $S_1N$.

Due to partial double-helix formation in the D DNA-Sephadex preparations, some antibodies with the above specificity may be included in the measurement for single-stranded DNA-binding immunoglobulins. Their relative contribution to this category could not be determined from the data present here. Since UV irradiation is employed during the preparation of DNA-Sephadex used here, the subsequent assay measurements of SLE sera may contain contribution from antibodies with such binding specificitions. The relative contribution is unknown but cannot be a major one. Calibration of a standard plasma. A standard SLE plasma (PS 33076) was calibrated for content of DNA-binding immunoglobulins with the aid of a different RIA assay for IgG and IgM. The latter calibration used a known reference serum IRP 67/95. Duplicate dilutions of PS 33076 (1:100, 1:200, 1:500, 1:1000, 1:2000) were tested with DNA-Sephadex A parallel series of tubes, to which no standard plasma dilutions had been added, were also prepared to be used with known quantities of IgM or IgG. The step in the assay in which $^{125}$I-GAH IgG, $^{131}$I-GAH IgM, and carrier were added was omitted and replaced by addition of 1 ml of buffer B. After the final 1 hr. incubation and washing steps, 0.5 ml of PBS-A containing 20 mM $MgCl_2$, 100 g/ml DNAse 1, and 1 mg/ml BSA was added to each tube to release DNA from the Sephadex. All tubes were incubated at 37° C. with agitation for 30 minutes. Control experiments showed this to be adequate time to remove all DNA from the DNA-Sephadex. To the series of tubes that did not contain plasma, dilutions of reference serum IRP 67/95 were then added to introduce a known amount of IgM and IgG into these tubes.

After thorough suspension, a mixture of solid-phase immunoabsorbents (Immunobead reagents; Bio-Rad Laboratories, Richmond, Calif.) was added to both sets of tubes for detection of IgG and IgM. The mixture included 2 mg of rabbit anti-human IgG Immunobeads (gamma chain-specific; capacity 0.48 g of IgG per milligram of beads) and 2 mg of rabbit anti-human IgM Immunobeads (mu chain-specific; capacity 1.35 mg of IgM per milligram of beads) in 1 ml of buffer B. The tubes were incubated for 1 hour at 37° C. with agitation and washed once with 10 ml of buffer B. Under these conditions, all IgM and IgG immunoglobulin attached to the Immunobeads.

To the washed pellets, 1 ml of a mixture of $^{125}$I-GAH IgG and $^{131}$I-GAH IgM (with diluted GAH IgG and GAH IgM antisera) was added to detect IgM and IgG on the pelleted beads. This $^{125}$I/$^{131}$I-labeled antibody solution was the same as that described above, except that the labels here were reversed. These labeled antibodies were preabsorbed against a mixture of the Immunobeads to remove reactivity against the rabbit reagents on the beads. The tubes were incubated 1 hour at 37° C. with agitation, washed twice, and counted. For construction of the standard curve, it was assumed that the input of immunoglobulins from the serum IRP dilutions (accurately known from data supplied with the ampule) were quantitively retained on the Immunobeads. This assumption was made because the input value of immunoglobulins was less than the capacity of the added Imunobeads and was confirmed inasmuch as no free IgG or IgM could be detected in the supernatants of these tubes.

Figure 1B:
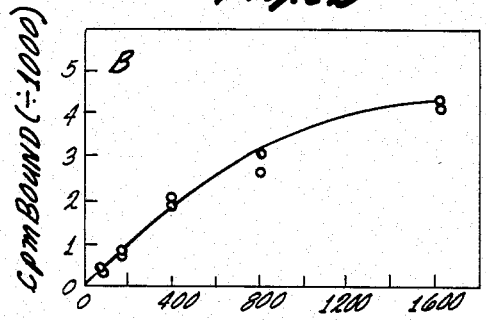

FIG. 1 shows the results obtained with the serum IRP dilutions in the calibration experiment described above. Dilutions of SLE plasma PS 33076, calibrated in this way, subsequently were used as the standards in all the assays. This obviated the need for continued use of costly solid-phase immunoabsorbents and serum IRP and was less time consuming. Dilutions of the SLE plasma standard indicated that the assay was fairly linear for IgM up to about 1000 ng bound and for the IgG up to 500 ng bound (FIGS. 1A and 1B).

Changes in DNA-binding immunoglobulin levels with disease activity in SLE. The data of FIGS. 5 and 6 (together with measurements of total serum immunoglobulins) and study of several cases of acute SLE reveal striking differences in the immunological assignments to the two DNA antigens between normal controls and SLE patients in exacerbation. Two patients recently studied showed roughly a 1000-fold increase in the fraction of serum IgM specific for double-stranded DNA over that seen for the normal serum pool. In both cases, the double-stranded DNA-binding IgM reached levels corresponding to 30% to 40% of the total circulating IgM. The double-stranded DNA-binding IgG also was increased in the SLE sera in comparison to normal serum pool; a 500-fold to 1000-fold increase in immunological assignment was observed, corresponding to 0.5% to 1.2% of the total circulating IgG. Less striking increases in the immunological assignments to single-stranded DNA-binding antibodies were observed.

Testing of random ambulatory SLE patients seen in an outpatient clinic was conducted in order to correlate clinical status with DNA antibody data as obtained by this procedure (FIG. 7). Consistent with the findings of others, antibody to single-stranded DNA predominated in most clinically active patients, but not all. In a few, such as Patients 1 and PS 33076 where all levels were evaluated, the antibody to double-stranded DNA was dominant. Although there were clinically active cases, it was not clear whether this association reflected a developmental aspect of the disease, i.e., a shift from single-stranded to double-stranded antibody at some phase, or a peculiarity of the individual patient.

The DNA-Sephadex assays were performed at the ionic strength of phosphate-buffered physiological saline in order to avoid artifactual binding of immunoglobulins to DNA at lower ionic strength. Glycerol and BSA were present in all assays to help reduce nonspecific protein binding and aggregation. EDTA and EGTA were present in all serum dilutions because human serum DNAses have been shown to require magnesium and/or calcium for in vitro activity. Measurement of the amount of DNA released from Sephadex after incubation with serum under the conditions used in the assay showed that less than 5% of the DNA was released spontaneously.

Summary. The method described above has certain important advantages. It provides for the attachment of DNA to a support and then the attachment of antibodies to the supported DNA. As one example, the antibodies may be those provided from serum lupus erythematosus (SLE) and may constitute the IgG and IgM immunoglobulins. The method also provides for the attachment of antigens (such as DNA) to a support and then the attachment of the IgG and IgM immunoglobulins to the supported antigen. By providing such attachments, an assay of the amount of the antibodies, or of the amount of the IgG and IgM immunoglobulins, in a serum can be facilitated.

Specialized assays of the antibodies can be provided by the method of this invention. For example, the attachment of the antibodies to native DNA and denatured DNA can be individually determined. The native DNA can even be treated to eliminate any single-stranded portions in the native (double-stranded) DNA. Separate determinations can be provided of the attachment of the IgG and IgM immunoglobulins to the supported DNA. Such attached immunoglobulins can then be quantitatively measured. The individual attachment of the IgG and IgM immunoglobulins to the supported native DNA and to the supported denatured DNA can also be determined by the assay methods of this invention.

Although this application has been disclosed and illustrated with reference to particular applications, the principles involved are susceptible of numerous other applications which will be apparent to persons skilled in the art. The invention is, therefore, to be limited only as indicated by the scope of the appended claims.

We claim:

1. In a method of testing for particular antibodies in the serum of a patient,
   providing a support,
   attaching DNA to the support,
   applying the serum to the supported DNA to obtain an attachment of the particular antibodies in the serum to the DNA with substantially no attachment of the particular antibodies in the serum to the support, and
   providing an assay to determine if the particular antibodies have been attached to the DNA.

2. In the method set forth in claim 1,
   the support constituting sephadex.

3. In the method set forth in claim 1, the particular antibodies constituting those produced by the patient when the patient has systemic lupus erythematosus.

4. In the method set forth in claim 1,
the antibodies in the serum being labelled prior to the application of the serum to the supported DNA.

5. In the method set forth in claim 4,
the attachment of the DNA to the support being facilitated by the irradiation of the DNA and the support with ultraviolet light.

6. In a method of testing for systemic lupus erythematosus antibodies in the serum of a patient,
provoiding a support,
attaching an antigen to the support,
supplying the serum to the supported antigen to obtain an attachment of the systemic lupus erythematosus antibodies substantially only to the supported antigen, and
providing an assay to determine the attachment of the systemic lupus erythematosus antibodies to the supported antigen.

7. In the method set forth in claim 6,
the support and the antigen being irradiated with ultraviolet light to facilitate the attachment of the antigen to the support.

8. In the method set forth in claim 6,
the systemic lupus erythematosus antibodies being radioactively labeled.

9. In a method as set forth in claim 6,
the systemic lupus erythematosus antibodies constituting IgG and IgM immunoglobulins and the assay providing an individual determination of the amount of the IgM immunoglobulin attached to the supported antigen and an individual determination of the amount of the IgG immunoglobulin attached to the supported antigen.

10. In the method set forth in claim 9,
the antigen constituting DNA.

11. In a method of testing for IgG and IgM systemic lupus erythematosus immunoglobulins in a serum of a patient,
providing a support,
attaching an antigen firmly to the support,
applying the serum to the supported antigen to obtain an attachment of IgG and IgM immunoglobulins substantially only to the supported antigen, and
providing an assay of the supported IgG and IgM immunoglobulins to determine the individual amount of the IgM immunoglobulin attached to the supported antigen and the individual amount of the IgG immunoglobulin attached to the supported antigen.

12. In a method as set forth in claim 11,
the antigen constituting DNA and the attachment of the DNA to the support being facilitated by irradiation with ultraviolet light.

13. In a method as set forth in claim 12,
the DNA constituting double-stranded and single-stranded DNA and the double-stranded DNA being treated to remove any single-stranded portions in the double-stranded DNA and the assay being provided to determine the individual amounts of the IgG and IgM immunoglobulins attached to the double-stranded DNA.

14. In a method as set forth in claim 13,
the assay providing an individual determination of the attachment of the IgM immunoglobulin to the supported double-stranded DNA and an individual determination of the attachment of the IgG immunoglobulin to the supported double-stranded DNA.

15. In a method as set forth in claim 14,
the support constituting sephadex and
the attachment of the DNA to the sephadex being facilitated by irradiation with ultraviolet light and
the double-stranded DNA being treated with an enzyme to remove any single-stranded portions in the double-stranded DNA before the assay.

16. In a method of testing for a particular antibody in the serum of a patient,
providing a support,
attaching double-stranded DNA to the support,
removing single-stranded portions from the supported double-stranded DNA,
attaching the particular antibody substantially only to the supported double-stranded DNA, and
providing an assay to determine the amount of the particular antibody attached to the supported double-stranded DNA.

17. In a method as set forth in claim 16,
the attachment of the DNA to the support being facilitated by irradiation with ultraviolet light, and
the single-stranded portions being removed from the supported double-stranded DNA by the addition of a particular enzyme.

18. In a method as set forth in claim 16,
the single-stranded portions being removed from the supported double-stranded DNA by the addition of a particular enzyme.

19. In a method as set forth in claim 16,
the particular antibody constituting IgG and IgM immunoglobulins and the assay individually identifying the amount of the IgM immunoglobulin attached to the supported double-stranded DNA and the amount of the IgG immunoglobulin attached to the supported double-stranded DNA.

20. In a method as set forth in claim 19,
the particular antibody constituting systemic lupus erythematosus and the immunoglobulins being designated as IgG and IGM.

21. In a method as set forth in claim 20,
the attachment of the DNA to the support being facilitated by irradiation with ultraviolet light and
the removal of the single-stranded portions from the supported double-stranded DNA being obtained by the addition of an enzyme.

22. In a method as set forth in claim 21,
the support constituting powdered sephadex.

23. In a method of testing for a particular antibody in the serum of a patient,
providing a support,
attaching a single-stranded DNA to the support,
attaching the particular antibody substantially only to the supported single-stranded DNA,
providing an assay to determine the amount of the antibody attached to the supported single-stranded DNA.

24. In a method set forth in claim 23,
providing a compensation in the assay for any double-stranded portions of DNA in the single-stranded DNA.

25. In a method as set forth in claim 24,
the particular antibody being produced by the patient when the patient has systemic lupus erythematosus and the particular antibody constituting IgG and IgM antibodies, the assay individually identifying the amount of the IgM immunoglobulin attached to the supported single-stranded DNA and the amount of the IgG immunoglobulin attached to the supported single-stranded DNA.

26. In a method as set forth in claim 23, the particular antibody being produced by the patient when the patient has systemic lupus erythematosus and the immunoglobulins being designated as IgG and IgM.

27. In a method as set forth in claim 26, the support constituting a cellulose and the attachment of the DNA to the support being facilitated by irradiation with ultraviolet light.

28. In the method set forth in claim 4, the DNA and the support being treated to faciliate the attachment of the DNA to the support.

29. In the method set forth in claim 6, the support and the antigen being treated to facilitate the attachment of the antigen to the support.

30. In the method set forth in claim 29, the antigen being single-stranded and double-stranded DNA and the assay being provided to determine the attachment of the systemic lupus erythematosus antibodies only to the double-stranded DNA.

31. In the method set forth in claim 29, the antigen being single-stranded and double-stranded and the assay being provided to determine the attachment of the systemic lupus erythematosus antibodies essentially only to the single-stranded DNA.

32. In the method set forth in claim 23, treating the single-stranded DNA and the support to facilitate the attachment of the single-stranded DNA to the support.

33. In the method set forth in claim 32, the support constituting a solid support and the antibody constituting systemic lupus erythematosus and the assay determining the individual amount of the IgM immunoglobuin attached to the supported single stranded DNA and the individual amount of the IgG immunoglobulin attached to the supported single-stranded DNA.

* * * * *